US008298552B2

(12) United States Patent
Kumar et al.

(10) Patent No.: US 8,298,552 B2
(45) Date of Patent: Oct. 30, 2012

(54) **ATTENUATED *MYCOPLASMA GALLISEPTICUM* STRAINS**

(75) Inventors: Mahesh Kumar, Portage, MI (US); Muhammad Ayub Khan, Mattawan, MI (US)

(73) Assignee: Wyeth LLC, Madison, NJ (US)

( * ) Notice: Subject to any disclaimer, the term of this patent is extended or adjusted under 35 U.S.C. 154(b) by 177 days.

(21) Appl. No.: 13/071,601

(22) Filed: Mar. 25, 2011

(65) Prior Publication Data

US 2011/0189099 A1 Aug. 4, 2011

Related U.S. Application Data

(62) Division of application No. 12/207,750, filed on Sep. 10, 2008, now Pat. No. 7,935,356.

(60) Provisional application No. 60/993,447, filed on Sep. 11, 2007.

(51) Int. Cl.
*A61K 39/02* (2006.01)

(52) U.S. Cl. ............... 424/264.1; 424/234.1; 424/185.1; 435/4; 435/29; 435/172.1; 435/252.1

(58) Field of Classification Search ........................ None
See application file for complete search history.

(56) References Cited

U.S. PATENT DOCUMENTS

| | | | |
|---|---|---|---|
| 5,064,647 | A | 11/1991 | Storm |
| 7,217,420 | B2 | 5/2007 | Kleven et al. |
| 2002/0187162 | A1 | 12/2002 | Geary et al. |
| 2006/0257414 | A1 | 11/2006 | Kleven et al. |

OTHER PUBLICATIONS

Papazisi et al (Microbiology. 2003. 149: 2307-2316.*
Papazisi, et al., "The complete genome sequence of the avian pathogan *Mycoplasma gallisepticum* strain $R_{low}$", Microbiology, vol. 149, pp. 2307-2316, 2003.

Mc Auliffe et al., "Differentiation of *Mycoplasma* Species by 16S Ribosomal DNA PCR and Denaturing Gradient Gel Electrophoresis Fingerprinting", J. Clin. Microbiol. vol. 41, pp. 4844-4847, 2003.
Mettifogo et al., "Molecular Characterization of MG Isolates Using RAPD and PFGE Isolated from Chickens in Brazil", J. Vet. Med., B-53, pp. 445-450, 2006.
Hudson et al., "Identification of a Virulence-Associated Dterminant, Dihydrolipoamide Dehydrogenase (*Ipd*), in *Mycoplasma gallisepticum* through In Vivo Screening of Transposon Mutants", Infection and Immunity, vol. 74, pp. 931-939, 2006.
NCBI Record for Protein Accession No. NP_852784, updated Jul. 21, 2008.
Adler, H. E., "Immunological Response to *Mycoplasma Gallisepticum*", Theriogenology, Aug.-Sep. 1976, vol. 6, No. 2-3, pp. 87-91.
Database UniProt [Online], Dec. 15, 2003, "SubName: Full-Putative uncharacterized protein;" XP-002506056, retrieved from EBI accession No. UNIPROT:Q7NC76, Database accession No. Q7NC76.
Gates, A.E., et al., "Comparative assessment of a metabolically attenuated *Mycoplasma gallisepticum* mutant as a live vaccine for the prevention of avian respiratory mycoplasmosis", Vaccine (2008), vol. 26, pp. 2010-2019.

* cited by examiner

*Primary Examiner* — Jennifer Graser
(74) *Attorney, Agent, or Firm* — Kelly M. Sullivan

(57) ABSTRACT

The present invention provides live, attenuated *Mycoplasma gallisepticum* bacteria that exhibit reduced expression of a protein identified as MGA_0621. In certain embodiments, the attenuated bacteria may additionally exhibit reduced expression of one or more proteins selected from the group consisting of pyruvate dehydrogenase, phosphopyruvate hydratase, 2-deoxyribose-5-phosphate aldolase, and ribosomal protein L35, relative to a wild-type *M. gallisepticum* bacterium. Also provided are vaccines and vaccination methods involving the use of the live, attenuated *M. gallisepticum* bacteria, and methods for making live attenuated *M. gallisepticum* bacteria. An exemplary live, attenuated strain of *M. gallisepticum* is provided, designated MGx+47, which was shown by proteomics analysis to exhibit significantly reduced expression of MGA_0621, and was shown to be safe and effective when administered as a vaccine against *M. gallisepticum* infection in chickens.

9 Claims, 1 Drawing Sheet

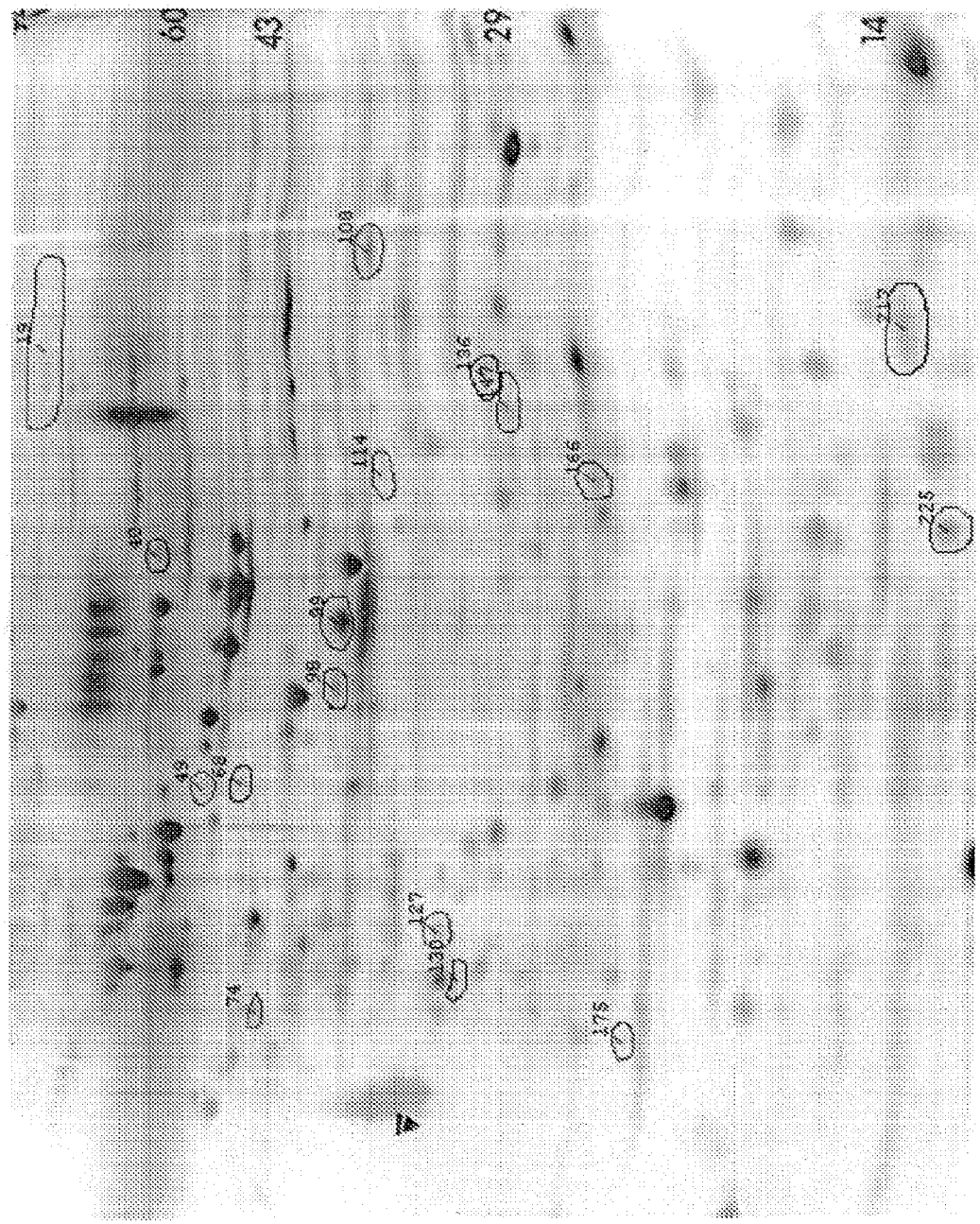

ATTENUATED *MYCOPLASMA GALLISEPTICUM* STRAINS

CROSS-REFERENCE TO RELATED APPLICATIONS

This application is a divisional application of U.S. application Ser. No. 12/207,750, filed Sep. 10, 2008 now U.S. Pat. No. 7,935,356 which claims priority to U.S. provisional application No. 60/993,447, filed Sep. 11, 2007. The entire disclosures are hereby incorporated by reference in their entirety.

FIELD OF THE INVENTION

The present invention relates to the fields of microbiology and immunology. More specifically, the invention relates to novel vaccines against bacterial pathogens.

BACKGROUND ART

Mycoplasmas are small prokaryotic organisms (0.2 to 0.3 μm) belonging to the class Mollicutes, whose members lack a cell wall and have a small genome size. The mollicutes include at least 100 species of *Mycoplasma*. *Mycoplasma* species are the causative agents of several diseases in human and non-human animals as well as in plants. *M. gallisepticum*, for example, is responsible for significant disease conditions in poultry. *M. gallisepticum* is associated with acute respiratory disease in chickens and turkeys and can also cause upper respiratory disease in game birds. In addition, *M. gallisepticum* has been recognized as a cause of conjunctivitis in house finches in North America.

An effective strategy for preventing and managing diseases caused by *M. gallisepticum* infection is by vaccination with live, attenuated strains of *M. gallisepticum* bacteria. The advantages of live attenuated vaccines, in general, include the presentation of all the relevant immunogenic determinants of an infectious agent in its natural form to the host's immune system, and the need for relatively small amounts of the immunizing agent due to the ability of the agent to multiply in the vaccinated host.

Live attenuated vaccine strains are often created by serially passaging a virulent strain multiple times in media. Although live attenuated vaccine strains against *M. gallisepticum* have been obtained by serial passaging, such strains are generally poorly characterized at the molecular level. It is assumed that attenuated strains made by serial passaging have accumulated mutations which render the microorganisms less virulent but still capable of replication. With regard to attenuated *M. gallisepticum* strains, however, the consequences of the mutations that result in attenuation (e.g., the identity of proteins whose expression pattern has been altered in the attenuated strain) are usually unknown.

Accordingly, a need exists in the art for new live, attenuated *M. gallisepticum* bacteria that have been characterized at the proteomic level and that are safe and effective in vaccine formulations.

BRIEF SUMMARY OF THE INVENTION

The present invention is based, in part, on the surprising discovery that *M. gallisepticum* bacteria that exhibit reduced expression of a polypeptide having the amino acid sequence of SEQ ID NO:1 are both safe and effective when used as a vaccine against *M. gallisepticum* infection in birds. The polypeptide of SEQ ID NO:1 is also referred to as "MGA_0621," and has NCBI Accession No. NP_852784.

Accordingly, the present invention is directed to live, attenuated *M. gallisepticum* bacteria that exhibit reduced expression of MGA_0621, relative to a wild-type *M. gallisepticum*. In a specific, non-limiting, exemplary embodiment, the invention provides a live, attenuated *M. gallisepticum* strain that exhibits reduced expression of MGA_0621, and further exhibits reduced expression of one or more proteins selected from the group consisting of pyruvate dehydrogenase, phosphopyruvate hydratase, 2-deoxyribose-5-phosphate aldolase, and ribosomal protein L35, relative to wild-type *M. gallisepticum* bacteria. According to certain embodiments of the present invention, the live, attenuated *M. gallisepticum* bacteria of the invention are characterized by proteomic analysis as having reduced expression of one or more of the aforementioned proteins. According to one exemplary embodiment of the present invention, the live attenuated *M. gallisepticum* strain is a strain that exhibits reduced expression of MGA_0621, pyruvate dehydrogenase, phosphopyruvate hydratase, 2-deoxyribose-5-phosphate aldolase, and ribosomal protein L35, relative to wild-type *M. gallisepticum* bacteria, which strain was deposited with the American Type Culture Collection (ATCC), P.O. Box 1549, Manassas, Va. 20108, on Jun. 19, 2007, and has been assigned Accession No. PTA-8485. This strain is alternatively referred to herein as "*M. gallisepticum* strain MGx+47," or "MG-P48".

The present invention also provides vaccine compositions comprising the live, attenuated *M. gallisepticum* bacteria of the invention, as well as methods of vaccinating an animal against *M. gallisepticum* infection.

In addition, the present invention provides methods for making and/or identifying attenuated *M. gallisepticum* clones. According to this aspect of the invention, the methods comprise subjecting an initial population of *M. gallisepticum* bacteria to attenuating conditions, assaying individual clones for reduced expression of MGA_0621, relative to a wild-type *M. gallisepticum*, and testing the clones for virulence. *M. gallisepticum* clones produced according to the methods of this aspect of the invention will exhibit reduced expression of MGA_0621, and may optionally exhibit reduced expression of one or more additional proteins selected from the group consisting of pyruvate dehydrogenase, phosphopyruvate hydratase, 2-deoxyribose-5-phosphate aldolase, and ribosomal protein L35. Preferably, the strains that exhibit reduced expression of at least one of the aforementioned proteins also exhibit reduced virulence relative to a wild-type *M. gallisepticum* bacterium.

BRIEF DESCRIPTION OF THE DRAWING

FIG. 1 is a photograph of a two-dimensional (2-D) polyacrylamide gel depicting protein spots of the attenuated *M. gallisepticum* strain MGx+47. Circled spots numbered 19, 49, 74, 108, 114, 127, 147, 166, 175 and 225 correspond to proteins that are up-regulated in MGx+47 relative to wild-type strain R-980. Circled spots numbered 40, 68, 98, 99, 130, 136 and 217 correspond to proteins that are down-regulated in MGx+47 relative to wild-type strain R-980.

DETAILED DESCRIPTION OF THE INVENTION

The present invention is directed to live, attenuated *M. gallisepticum* bacteria that are suitable for use in vaccine formulations. The *M. gallisepticum* bacteria of the present invention exhibit reduced expression of a protein referred to as MGA_0621. In certain embodiments, the *M. gallisepti-

*cum* bacteria of the invention further exhibit reduced expression of one or more additional proteins selected from the group consisting of pyruvate dehydrogenase, phosphopyruvate hydratase, 2-deoxyribose-5-phosphate aldolase, and ribosomal protein L35, relative to the expression of these proteins in a wild-type *M. gallisepticum* bacterium of the same species.

MGA_0621 is identified under NCBI Accession No. NP_852784 has the following 162 amino acid sequence:

```
                                          (SEQ ID NO: 1)
MTRTMKNKKAKKKERRFTDLSADLDEEVEKIDPEYEDFKEIKIEKNKDN

QVIDKNDPFFYSESFEEARIQLIKDKKVEVKKEEEKVQETTVKNKISEA

KKEEAKDVYIDSSLEIASQEPLTKGMHFYTNSRIIRKVRECAKNKGLSI

SRLITMILDKSIKEE..
```

Reduced Expression of *Mycoplasma Gallisepticum* Proteins

A person of ordinary skill in the art will be able to determine, using routine molecular biological techniques, whether an attenuated *M. gallisepticum* bacterium exhibits reduced expression of one or more proteins that are normally expressed in wild-type *M. gallisepticum* bacterial cells. Determining whether an attenuated bacterium exhibits reduced expression of a particular protein (e.g., MGA_0621, pyruvate dehydrogenase, phosphopyruvate hydratase, 2-deoxyribose-5-phosphate aldolase, ribosomal protein L35, etc.), relative to a wild-type bacterium, can be accomplished by several methods known in the art. Exemplary methods include, e.g., quantitative antibody-based methods such as Western blotting, radioimmunoassays (RIAs), and enzyme-linked immunosorbant assays (ELISAs), in which an antibody is used which detects and binds to the protein of interest. In addition, since messenger RNA (mRNA) levels generally reflect the quantity of the protein encoded therefrom, quantitative nucleic acid-based methods may also be used to determine whether an attenuated *M. gallisepticum* bacterium exhibits reduced expression of one or more proteins. For example, quantitative reverse-transcriptase/polymerase chain reaction (RT-PCR) methods may be used to measure the quantity of mRNA corresponding to a particular protein of interest. Numerous quantitative nucleic acid-based methods are well known in the art.

The following is a non-limiting, exemplary method that can be used for determining whether an attenuated *M. gallisepticum* bacterium exhibits reduced expression of a protein such as, e.g., MGA_0621.

First, a population of attenuated *M. gallisepticum* cells and a population of wild-type *M. gallisepticum* cells are grown under substantially identical conditions in substantially the same culture medium. Next, the two populations of cells are subjected to cell-disrupting conditions. The disrupted cells (or the protein-containing fractions thereof) are subjected, in parallel, to SDS polyacrylamide gel electrophoresis (SDS-PAGE) and then to Western blotting using an antibody which binds to the *M. gallisepticum* MGA_0621 protein (such antibodies can be obtained using standard methods that are well known in the art). A labeled secondary antibody is then applied in order to provide a measurable signal that is proportional to the amount of the protein derived from the cells. If the amount of signal exhibited by the attenuated *M. gallisepticum* strain is less than the amount of signal exhibited by the wild-type *M. gallisepticum* strain, then it can be concluded that the attenuated strain exhibits reduced expression of MGA_0621 relative to the wild-type strain. Variations on this exemplary method, as well as alternatives thereto, will be immediately evident to persons of ordinary skill in the art.

The present invention includes attenuated *M. gallisepticum* bacteria that exhibit any degree of reduction in expression of a protein (e.g., MGA_0621, pyruvate dehydrogenase, phosphopyruvate hydratase, 2-deoxyribose-5-phosphate aldolase, ribosomal protein L35, etc.) compared to the expression of that protein observed in a wild-type strain. In certain embodiments, the attenuated bacterium exhibits at least about 5% less expression of the protein relative to a wild-type bacterium. As an example, if a given quantity of a wild-type *M. gallisepticum* strain exhibit 100 units of expression of a particular protein and the same quantity of a candidate attenuated *M. gallisepticum* strain exhibits 95 units of expression of the protein, then it is concluded that the attenuated strain exhibits 5% less expression of the protein relative to the wild-type bacterium (additional examples for calculating "percent less expression" are set forth elsewhere herein). In certain other embodiments, the attenuated bacterium exhibits at least about 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99% less expression of the protein relative to a wild-type *M. gallisepticum* bacterium. In yet other embodiments, the attenuated *M. gallisepticum* strain exhibits no expression (i.e., 100% less expression) of the protein relative to a wild-type *M. gallisepticum* bacterium.

In certain exemplary embodiments of the present invention, the attenuated bacteria exhibit at least 5% less expression of MGA_0621, and optionally at least 5% less expression of one or more proteins selected from the group consisting of pyruvate dehydrogenase, phosphopyruvate hydratase, 2-deoxyribose-5-phosphate aldolase, and ribosomal protein L35, relative to a wild-type *M. gallisepticum* bacterium.

As used herein, the "percent less expression" of a particular protein exhibited by an attenuated *M. gallisepticum* strain relative to a wild-type strain is calculated by the following formula: $(A-B)/A \times 100$; wherein A=the relative level of expression of the protein in a wild-type *M. gallisepticum* strain; and B=the relative level of expression of the protein in the attenuated strain. Solely for the purpose of illustration, if a wild-type *M. gallisepticum* strain exhibited 0.2500 units of expression of protein "Y", and an attenuated strain of *M. gallisepticum* exhibited 0.1850 units of expression of protein "Y" then the attenuated strain is said to exhibit $[(0.2500-0.1850)/0.2500 \times 100]=26\%$ less expression of protein "Y" relative to the wild-type strain. Table 5 in Example 3 herein provides additional illustrative examples of percent less expression calculated for an exemplary attenuated strain of *M. gallisepticum* relative to a wild-type *M. gallisepticum* strain.

Vaccine Compositions

The present invention also includes vaccine compositions comprising a live, attenuated *M. gallisepticum* bacterium of the invention and a pharmaceutically acceptable carrier. As used herein, the expression "live, attenuated *M. gallisepticum* bacterium of the invention" encompasses any live, attenuated *M. gallisepticum* bacterium that is described and/or claimed elsewhere herein. The pharmaceutically acceptable carrier can be, e.g., water, a stabilizer, a preservative, culture medium, or a buffer. Vaccine formulations comprising the attenuated *M. gallisepticum* bacteria of the invention can be prepared in the form of a suspension or in a lyophilized form or, alternatively, in a frozen form. If frozen, glycerol or other similar agents may be added to enhance stability when frozen.

Methods of Vaccinating an Animal

The present invention also includes methods of vaccinating an animal against *M. gallisepticum* infection. The methods according to this aspect of the invention comprise administering to an animal an immunologically-effective amount of a vaccine composition comprising a live, attenuated *M. gallisepticum* bacterium of the invention. As used herein, the expression "live, attenuated *M. gallisepticum* bacterium of the invention" encompasses any live, attenuated *M. gallisepticum* bacterium that is described and/or claimed elsewhere herein. The expression "immunologically-effective amount" means that amount of vaccine composition required to invoke the production of protective levels of antibodies in an animal upon vaccination. The vaccine composition may be administered to the animal in any manner known in the art including oral, intranasal, mucosal, topical, transdermal, and parenteral (e.g., intravenous, intraperitoneal, intradermal, subcutaneous or intramuscular) routes. Administration can also be achieved using needle-free delivery devices. Administration can be achieved using a combination of routes, e.g., first administration using a parental route and subsequent administration using a mucosal route, etc.

The animal to which the attenuated *M. gallisepticum* strain is administered is preferably a bird, e.g., a chicken or a turkey. Where the animal is a bird, the vaccine formulations of the invention may be administered such that the formulations are immediately or eventually brought into contact with the bird's respiratory mucosal membranes. Thus, the vaccine formulations may be administered to birds, e.g., intranasally, orally, and/or intraocularly. The vaccine compositions for avian administration may be formulated as described above and/or in a form suitable for administration by spray, including aerosol (for intranasal administration) or in drinking water (for oral administration).

Vaccine compositions of the present invention that are administered by spray or aerosol can be formulated by incorporating the live, attenuated *M. gallisepticum* bacteria into small liquid particles. The particles can have an initial droplet size of between about 10 µm to about 100 µm. Such particles can be generated by, e.g., conventional spray apparatus and aerosol generators, including commercially available spray generators for knapsack spray, hatchery spray and atomist spray.

Methods for Making Attenuated *M. Gallisepticum* Clones

In another aspect of the present invention, the invention provides methods for identifying and/or making attenuated *M. gallisepticum* clones. The methods according to this aspect of the invention comprise subjecting an initial population of *M. gallisepticum* bacteria to attenuating conditions, thereby producing a putatively attenuated bacterial population. Next, individual clones of the putatively attenuated bacterial population are assayed for reduced expression of MGA_0621, relative to a wild-type *M. gallisepticum* bacterium. The clones that are identified as having reduced expression of MGA_0621 are then tested for virulence. Clones that exhibit both reduced expression of MGA_0621 and reduced virulence relative to a wild-type *M. gallisepticum* bacterium are identified as attenuated *M. gallisepticum* clones.

According to this aspect of the invention, the "initial population of *M. gallisepticum* bacteria" can be any quantity of *M. gallisepticum* bacteria. The bacteria, in certain embodiments are wild-type bacteria. Alternatively, the bacteria may contain one or more mutations. Preferably, however, the bacteria in the initial population are clonally identical or substantially clonally identical; that is, the bacteria preferably are all derived from a single parental *M. gallisepticum* bacterial cell and/or have identical or substantially identical genotypic and/or phenotypic characteristics.

As used herein, the term "attenuating conditions" means any condition or combination of conditions which has/have the potential for introducing one or more genetic changes (e.g., nucleotide mutations) into the genome of a *M. gallisepticum* bacterium. Exemplary, non-limiting, attenuating conditions include, e.g., passaging bacteria in culture, transforming bacteria with a genome-insertable genetic element such as a transposon (e.g., a transposon that randomly inserts into the *M. gallisepticum* genome), exposing bacteria to one or more mutagens (e.g., chemical mutagens or ultraviolet light), etc. When bacterial cells are attenuated by passaging in vitro, the cells may be passaged any number of times, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more times in vitro.

The initial population of *M. gallisepticum* cells, after being subjected to attenuating conditions, are referred to herein as a putatively attenuated bacterial population. Individual clones of the putatively attenuated bacterial population can be obtained by standard microbiological techniques including, e.g., serially diluting the cells and plating out individual cells on appropriate media. Once obtained, the individual clones of the putatively attenuated bacterial population are assayed for reduced expression of MGA_0621 and/or one or more additional specified proteins. Methods for determining whether an attenuated *M. gallisepticum* bacterium exhibits reduced expression of one or more proteins that are normally expressed in wild-type *M. gallisepticum* bacterial cells are described elsewhere herein. Exemplary methods include, e.g., RT-PCR-based methods, Western blot, etc.

Individual clones that are identified as having reduced expression of MGA_0621 can be tested for virulence by administration of the clones to an animal that is susceptible to infection by the wild-type (unattenuated) version of the bacterium. As used herein, "an animal that is susceptible to infection by a wild-type *M. gallisepticum* bacterium" is an animal that shows at least one clinical symptom after being challenged with a wild-type *M. gallisepticum* bacterium. Such symptoms are known to persons of ordinary skill in the art. For example, in the case of a putatively attenuated *M. gallisepticum* strain that exhibits reduced expression of, e.g., MGA_0621, the strain can be administered to, e.g., turkeys or chickens (which are normally susceptible to infection by wild-type *M. gallisepticum*). Clinical symptoms of *M. gallisepticum* infection of poultry animals include, e.g., acute respiratory symptoms, pericarditis, perihepatitis, air sacculitis, trachea thickening, reduced weight gain, deciliation, abnormal goblet cells, capillary distension, increased numbers of lymphocytes, plasma cells and/or heterophils, and in some cases reduced egg production. Thus, if the putatively attenuated *M. gallisepticum* strain, when administered to a chicken or turkey, results in fewer and/or less severe symptoms as compared to a turkey or chicken that has been infected with a wild-type *M. gallisepticum* strain, then the putatively attenuated *M. gallisepticum* strain is deemed to have "reduced virulence." Any degree of reduction in symptoms will identify the putatively attenuated strain as having reduced virulence. In certain embodiments, the putatively attenuated strain will be avirulent.

According to the present invention, an *M. gallisepticum* clone that exhibits reduced expression of MGA_0621 (and/or one or more additional specified proteins), and that exhibits reduced virulence relative to a wild-type *M. gallisepticum* bacterium is an attenuated *M. gallisepticum* clone. An exemplary, live, attenuated *M. gallisepticum* clone of the present invention, which exhibits reduced expression of MGA_0621 (along with reduced expression of pyruvate dehydrogenase, phosphopyruvate hydratase, 2-deoxyribose-5-phosphate aldolase, and ribosomal protein L35) is the strain designated MGx+47. MGx+47 has been deposited with the American Type Culture Collection, P.O. Box 1549, Manassas, Va. 20108, on Jun. 19, 2007 and was assigned accession number PTA-8485.

The following examples are illustrative, but not limiting, of the method and compositions of the present invention. Other suitable modifications and adaptations of the variety of conditions and parameters normally encountered in molecular biology and chemistry which are obvious to those skilled in the art in view of the present disclosure are within the spirit and scope of the invention.

EXAMPLES

Example 1

Generation of a Live, Attenuated *M. Gallisepticum* Strain

A new live, attenuated *Mycoplasma gallisepticum* strain was generated by passaging a wild-type *M. gaffiespticum* strain R980 multiple times in vitro. In particular, 0.1 mL seed material of wild-type *M. gallisepticum* strain R-980 was inoculated into 20 mL of modified Frey's medium (Frey et al., Am. J. Vet. Res. 29:2163-2171 (1968) (also referred to herein as "MG culture medium"). The wild-type cells were grown until media color changed to bright yellow. The bright yellow cultures were subsequently used to re-inoculate fresh MG culture media as described above. The culture was passaged a total of 47 times in this manner. The resulting strain was tested for attenuation by vaccinating groups of birds followed by challenge using the wild-type *M. gallisepticum*. All the birds were necropsized two weeks post-challenge and mycoplasma related pathologies were observed. High passage strain (x+47) provided protection against the clinical signs associated with *Mycoplasma gallisepticum* infection. This attenuated *M. gallisepticum* strain designated MGx+47 was deposited with the American Type Culture Collection, P.O. Box 1549, Manassas, Va. 20108, on Jun. 19, 2007 and was assigned accession number PTA-8485.

Example 2

Safety and Efficacy Evaluation of a Live, Attenuated *M. gallisepticum* Vaccine in Chickens In this Example, the safety and efficacy of the new *M. gallisepticum* vaccine strain MGx+47 obtained in Example 1 was assessed in chickens.

Seventy one SPF white leghorn chickens were divided into seven groups as follows:

TABLE 1

Study Design

| Group | # Chickens | Vaccinated | Challenged |
|---|---|---|---|
| 1 | 11 | No | Yes |
| 2 | 10 | Yes | No |
| 3 | 11 | Yes | Yes |
| 4a | 10 | Yes | No |
| 4b | 11 | Yes | No |
| 4c | 9 | Yes | No |
| 5 | 9 | No | No |

The chickens in groups 2, 3, 4a, 4b and 4c were vaccinated with attenuated strain MGx+47 at $3.62 \times 10^7$ CCU/mL/bird, administered by coarse spray at 4 weeks of age. The chickens in groups 1 and 3 were challenged intratracheally (IT) at 7 weeks of age with 0.5 mL of *Mycoplasma gallisepticum* strain R at $7.74 \times 10^5$ CCU/mL. Necropsy was performed on the chickens of groups 1, 2, 3 and 5 at 9 weeks of age, and necropsy was performed on the chickens of groups 4a, 4b and 4c at 7, 14 and 21 days post vaccination (DPV), respectively. The chickens were assessed for average weight gain, pericarditis, perihepatitis, airsacculitis, and tracheitis. The results are summarized in Table 2.

TABLE 2

Safety and Efficacy Summary
Vaccination = $3.62 \times 10^7$ CFU/mL/bird
Challenge = 0.5 mL at $7.74 \times 10^5$ CFU/mL

| Group | Vaccinated | Challenged | Average Weight Gain (kg/day) | Pericarditis | Perihepatitis | Airsacculitis | Airsacculitis Score (average of positives) | Trachea (Histology) |
|---|---|---|---|---|---|---|---|---|
| 1 | No | Yes | 0.016 | 0/11 | 0/11 | 9/11 | 3.56 | severe tracheitis |
| 2 | Yes | No | 0.018 | 0/10 | 0/10 | 0/10 | 0 | normal |
| 3 | Yes | Yes | 0.017 | 0/11 | 0/11 | 2/11 | 2.5 | mixed tracheitis |
| 4a | Yes | No | 0.016 | 0/9 | 0/9 | 0/9 | 0 | normal |
| 4b | Yes | No | 0.017 | 0/11 | 0/11 | 0/11 | 0 | normal |
| 4c | Yes | No | 0.017 | 0/10 | 0/10 | 0/10 | 0 | normal |
| 5 | No | No | 0.015 | 0/9 | 0/9 | 0/9 | 0 | normal |

TABLE 3

Safety Table: Histology Report of Formalin-Fixed Chicken Tracheas from Individual Vaccinated/Unchallenged Chickens (Group 4a, 4b and 4c)

| Time Point | Chicken | Cilia | Goblet Cells/M | Capillary Distension | LC/PC | PMNs | Thickness (microns) |
|---|---|---|---|---|---|---|---|
| 7 DPV | 1 | N | – | – | – | – | 30 |
|  | 2 | N | – | – | – | – | 30 |

TABLE 3-continued

Safety Table: Histology Report of Formalin-Fixed Chicken Tracheas from Individual Vaccinated/Unchallenged Chickens (Group 4a, 4b and 4c)

| Time Point | Chicken | Cilia | Goblet Cells/M | Capillary Distension | LC/PC | PMNs | Thickness (microns) |
|---|---|---|---|---|---|---|---|
|  | 3 | N | – | – | – | – | 30 |
|  | 4 | N | – | – | + | – | 30 |
|  | 5 | N | – | – | – | – | 30 |
|  | 6 | N | – | – | + | – | 30 |
|  | 7 | N | – | – | + | – | 30 |
|  | 8 | N | – | – | – | – | 30 |
|  | 9 | N | + | – | – | – | 30 |
| 14 DPV | 1 | N | – | – | – | – | 50 |
|  | 2 | N | + | – | – | – | 50 |
|  | 3 | N | – | – | + | – | 50 |
|  | 4 | N | – | – | – | – | 50 |
|  | 5 | N | – | – | – | – | 50 |
|  | 6 | N | – | – | – | – | 50 |
|  | 7 | N | – | – | – | – | 50 |
|  | 8 | N | – | – | – | – | 50 |
|  | 9 | N | – | – | + | – | 50 |
|  | 10 | N | – | – | – | – | 50 |
|  | 11 | N | – | – | + | – | 50 |
| 21 DPV | 1 | N | – | – | – | – | 50 |
|  | 2 | N | – | – | ++ | – | 110 |
|  | 3 | N | – | – | – | – | 50 |
|  | 4 | N | – | – | – | – | 50 |
|  | 5 | N | – | – | – | – | 50 |
|  | 6 | N | – | – | + | – | 50 |
|  | 7 | N | – | – | – | – | 50 |
|  | 8 | N | – | – | – | – | 50 |
|  | 9 | N | – | – | – | – | 50 |
|  | 10 | N | – | – | – | – | 50 |

TABLE 4

Efficacy Table: Histology Report of Formalin-Fixed Chicken Tracheas from Individual Chickens

| Group | Chicken | Cilia | Goblet Cells/M | Capillary Distension | LC/PC | PMNs | Thickness (microns) |
|---|---|---|---|---|---|---|---|
| 1 | | | Not Vaccinated; Challenged | | | | |
|  | 1 | – | + | ++ | ++++ | ++ | 410 |
|  | 2 | +/– | – | – | + | – | 90 |
|  | 3 | N | + | – | – | – | 50 |
|  | 4 | – | – | ++++ | ++++ | – | 420 |
|  | 5 | N | + | + | + | – | 60 |
|  | 6 | – | + | ++++ | ++++ | +++ | 400 |
|  | 7 | – | – | ++++ | ++++ | – | 440 |
|  | 8 | – | – | ++++ | ++++ | ++++ | 280 |
|  | 9 | – | + | – | – | – | 40 |
|  | 10 | – | – | ++++ | ++++ | – | 260 |
|  | 11 | – | + | ++++ | ++++ | +++ | 450 |
| 3 | | | Vaccinated and Challenged | | | | |
|  | 1 | – | – | ++ | ++++ | – | 380 |
|  | 2 | N | – | + | + | – | 40 |
|  | 3 | N | – | + | + | – | 50 |
|  | 4 | – | – | + | +++ | ++ | 220 |
|  | 5 | N | – | + | + | – | 60 |
|  | 6 | N | – | + | + | – | 60 |
|  | 7 | N | – | – | – | – | 50 |
|  | 8 | N | – | – | – | – | 50 |
|  | 9 | N | – | + | + | – | 50 |
|  | 10 | +/– | – | + | ++ | – | 140 |
| 5 | | | Not Vaccinated; Not Challenged | | | | |
|  | 1 | N | – | – | + | – | 50 |
|  | 2 | N | – | – | + | – | 50 |
|  | 3 | N | – | – | – | – | 50 |
|  | 4 | N | – | – | + | – | 50 |
|  | 5 | N | – | – | – | – | 50 |
|  | 6 | N | – | – | + | – | 50 |
|  | 7 | N | – | – | – | – | 50 |
|  | 8 | N | – | – | + | – | 50 |
|  | 9 | N | – | – | – | – | 50 |

Key to Safety and Efficacy Tables (Tables 3 and 4):
  All "vaccinated" birds were vaccinated by coarse spray with vaccine strain MGx+47 at $3.62 \times 10^7$ CCU/mL/bird;
  All "challenged" birds were challenged intratracheally (IT) with 0.5 mL of *Mycoplasma gallisepticum* strain R at $7.74 \times 10^5$ CCU/mL
  Time Point (in Table 3: Safety Table)=number of days after vaccination when the chickens were examined, expressed as # days post vaccination (DPV).
  Cilia: "N"=normal cilia; "–"=deciliation;
  Goblet Cells/M ("–"=normal goblet cells; "+"=mucus lying on the respiratory surface);
  Capillary Distension ("–"=no distension or inflammation; "+"=moderate capillary distension or inflammation; "++"=severe capillary distension or inflammation);
  LC/PC=Lymphocytes and Plasma cells ("–"=none; "+"=few; "++++"=numerous);
  PMNs=Heterophils ("–"=none; "+"=few; "++++"=numerous);

The histology analysis of the group 2 chickens (vaccinated but not challenged) was substantially similar to that of the group 5 chickens (unvaccinated, unchallenged), demonstrating the safety of the newly generated MGx+47 vaccine strain. (See, e.g., Table 2 above).

With regard to efficacy, the group 3 chickens (vaccinated and challenged) showed significantly reduced airsacculitis compared to the group 1 chickens (unvaccinated and challenged). (See, e.g., Tables 2 and 4). In addition, as illustrated in Table 4, the group 3 chickens exhibited fewer histological signs of *M. gallisepticum* infection with regard to cilia, goblet cells, capillary distension, lymphocytes and plasma cells (LC/PC), heterophils (PMNs) and trachea thickness. (See Table 4).

Thus, this Example demonstrates that MGx+47 is a safe and effective live, attenuated *M. gallisepticum* vaccine strain.

Example 3

Proteomic Characterization of MGx+47 Vaccine Strain

In an effort to more precisely define the MGx+47 vaccine strain (see Examples 1 and 2) at the molecular level, a proteomic analysis of this strain was undertaken.

In this Example, total protein was isolated from the wild-type *M. gallisepticum* strain R-980 and from the newly identified vaccine strain MGx+47. Proteins from each strain were resolved by 2-dimensional polyacrylamide gel electrophoresis followed by computerized analysis of the gel images. (See FIG. 1). Protein spots were identified that were differentially expressed in the vaccine strain. Protein spots that were absent, or were expressed at significantly reduced levels, in the vaccine strain compared to the wild-type strain were excised from the gel.

Five spots were identified that were expressed at significantly lower levels in the MGx+47 vaccine strain as compared to the wild-type *M. gallisepticum*. Each of these protein spots were excised from the gel and enzmatically digested. Followed by peptide mass fingerprinting using matrix-assisted laser desorption/ionization-time of flight mass spectrometry (MALDI-TOF MS). The mass spectra identified for each protein spot was compared to a peptide mass database to identify the proteins and the corresponding genes that encodes them. The results of this analysis are summarized in the Table below:

TABLE 5

Summary of Proteomic Analysis of MGx + 47

| Gene | Product | Function | Level of expression in wild-type MG | Level of expression in MGx + 47 | Percent decrease in expression |
|---|---|---|---|---|---|
| acoA | Pyruvate dehydrogenase | Required for energy production and conversion (Kreb's Cycle) | 0.1872 | 0.0858 | 54.2% |
| eno | Phospho-pyruvate hydratase | Catalyzes the formation of phosphoenol-pyruvate | 0.0683 | 0.0173 | 74.7% |
| deoC | 2-deoxyribose-5-phosphate aldolase | Required for nucleotide metabolism | 0.0525 | 0.0309 | 41.1% |
| rpml | Ribosomal protein L35 | Translation, ribosomal structure and biogenesis | 0.1171 | 0.0259 | 77.9% |
| MGA_0621 | Hypothetical protein | Unknown | 0.4534 | 0.0835 | 81.6% |

The decrease in expression of the gene products can also be expressed in terms of "fold decrease in expression." For example, in Table 5, strain MGx+47 can be said to exhibit 2.2, 3.9, 1.7, 4.5 and 5.4 fold decreased expression of acoA, eno, deoC, rpml, and MGA_0621, respectively, relative to wild-type MG.

As indicated in Table 5, five gene products were identified that had significantly reduced expression in the live, attenuated MGx+47 vaccine strain as compared to the wild-type R-980 strain: AcoA, Eno, DeoC, Rmpl, and MGA_0621 (a hypothetical protein identified under NCBI accession number NP_852784). The largest decrease in expression was observed for MGA_0621. Thus, mutations or growth conditions which cause a decrease in MGA_0621 expression are likely to result in attenuation of *M. gallisepticum*. Down regulation of MGA_0621, therefore, appears to be a effective strategy for producing attenuated strains of *M. gallisepticum*.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A method for identifying attenuated *Mycoplasma gallisepticum* clones, said method comprising:
   a. subjecting an initial population of *Mycoplasma gallisepticum* bacteria to attenuating conditions, thereby producing a putatively attenuated bacterial population; and
   b. assaying individual clones of said putatively attenuated bacterial population for reduced expression of a protein having the amino acid sequence of SEQ ID NO:1, relative to a wild-type *Mycoplasma gallisepticum*; and
   c. testing clones identified in (b) as having reduced expression of said protein for virulence;
   wherein a *Mycoplasma gallisepticum* clone that exhibits reduced expression of said protein and reduced virulence relative to a wild-type *Mycoplasma gallisepticum* is an attenuated *Mycoplasma gallisepticum* clone.

2. The method of claim 1, wherein said attenuating conditions of (a) comprise passaging said initial population of *Mycoplasma gallisepticum* bacteria at least 2 times in vitro.

3. The method of claim 2, wherein said attenuating conditions of (a) comprise passaging said initial population of *Mycoplasma gallisepticum* bacteria at least 5 times in vitro.

4. The method of claim 3, wherein said attenuating conditions of (a) comprise passaging said initial population of *Mycoplasma gallisepticum* bacteria at least 10 times in vitro.

5. The method of claim 1, wherein said attenuating conditions of (a) comprise transforming said initial population of *Mycoplasma gallisepticum* with a transposon which randomly inserts into the *Mycoplasma gallisepticum* genome.

6. The method of claim 1, wherein said attenuating conditions of (a) comprise exposing said initial population of *Mycoplasma gallisepticum* to a chemical mutagen or ultra violet light.

7. The method of claim 1, wherein said individual clones of said putatively attenuated bacterial population are assayed in (b) for reduced expression of said protein by reverse transcriptase-polymerase chain reaction (RT-PCR).

8. The method of claim 1, wherein said individual clones of said putatively attenuated bacterial population are assayed in (b) for reduced expression of said protein by Western blot.

9. The method of claim 1, wherein said clones identified in (b) are tested for virulence in (c) by administering one or more of said clones to an animal that is susceptible to *Mycoplasma gallisepticum* infection and comparing the clinical symptoms observed in said animals after being administered said one or more clones to the clinical symptoms of control animals that are not administered said clones.

* * * * *

```
SEQUENCE LISTING

<160> NUMBER OF SEQ ID NOS: 1

<210> SEQ ID NO 1
<211> LENGTH: 162
<212> TYPE: PRT
<213> ORGANISM: Mycoplasma gallisepticum

<400> SEQUENCE: 1

Met Thr Arg Thr Met Lys Asn Lys Lys Ala Lys Lys Lys Glu Arg Arg
1               5                   10                  15

Phe Thr Asp Leu Ser Ala Asp Leu Asp Glu Glu Val Glu Lys Ile Asp
                20                  25                  30

Pro Glu Tyr Glu Asp Phe Lys Glu Ile Lys Ile Glu Lys Asn Lys Asp
            35                  40                  45

Asn Gln Val Ile Asp Lys Asn Asp Pro Phe Phe Tyr Ser Glu Ser Phe
        50                  55                  60

Glu Glu Ala Arg Ile Gln Leu Ile Lys Asp Lys Lys Val Glu Val Lys
65                  70                  75                  80

Lys Glu Glu Glu Lys Val Gln Glu Thr Thr Val Lys Asn Lys Ile Ser
                85                  90                  95

Glu Ala Lys Lys Glu Glu Ala Lys Asp Val Tyr Ile Asp Ser Ser Leu
            100                 105                 110
```

```
Glu Ile Ala Ser Gln Glu Pro Leu Thr Lys Gly Met His Phe Tyr Thr
        115                 120                 125

Asn Ser Arg Ile Ile Arg Lys Val Arg Glu Cys Ala Lys Asn Lys Gly
    130                 135                 140

Leu Ser Ile Ser Arg Leu Ile Thr Met Ile Leu Asp Lys Ser Ile Lys
145                 150                 155                 160

Glu Glu
```